(12) United States Patent
Zhou et al.

(10) Patent No.: US 10,247,642 B2
(45) Date of Patent: Apr. 2, 2019

(54) PORTABLE EFFICIENT MAGNETIC SOLID PHASE EXTRACTION DEVICE AND EXTRACTION METHOD THEREOF

(71) Applicant: NANJING UNIVERSITY, Nanjing (CN)

(72) Inventors: Qing Zhou, Nanjing (CN); Wei Wang, Nanjing (CN); Aimin Li, Nanjing (CN); Qingqing Zhao, Nanjing (CN); Minglu Wang, Nanjing (CN); Rui Gao, Nanjing (CN); Xiaowen Ma, Nanjing (CN); Peng Shi, Nanjing (CN); Xun Chen, Nanjing (CN)

(73) Assignee: NANJING UNIVERSITY, Nanjing (CN)

( * ) Notice: Subject to any disclaimer, the term of this patent is extended or adjusted under 35 U.S.C. 154(b) by 150 days.

(21) Appl. No.: 15/619,456

(22) Filed: Jun. 10, 2017

(65) Prior Publication Data
US 2017/0276576 A1 Sep. 28, 2017

(30) Foreign Application Priority Data
Aug. 29, 2016 (CN) .......................... 2016 1 0782755

(51) Int. Cl.
| | |
|---|---|
| G01N 1/18 | (2006.01) |
| G01N 30/14 | (2006.01) |
| G01N 1/40 | (2006.01) |
| B03C 1/033 | (2006.01) |
| B03C 1/28 | (2006.01) |
| G01N 1/10 | (2006.01) |

(52) U.S. Cl.
CPC ............. G01N 1/18 (2013.01); B03C 1/0335 (2013.01); B03C 1/288 (2013.01); G01N 1/405 (2013.01); G01N 30/14 (2013.01); *B03C 2201/18* (2013.01); *G01N 2001/1025* (2013.01)

(58) Field of Classification Search
CPC .......... G01N 1/18; G01N 30/14; G01N 1/405; G01N 2001/1025; B03C 1/288; B03C 1/0335; B03C 2201/18
See application file for complete search history.

(56) References Cited

U.S. PATENT DOCUMENTS

2002/0098594 A1* 7/2002 Sandra ..................... G01N 1/34
436/161

* cited by examiner

*Primary Examiner* — Xin Y Zhong
(74) *Attorney, Agent, or Firm* — CBM Patent Consulting, LLC

(57) ABSTRACT

A device comprises a contact reaction chamber, a circulating water inlet, a clear water basin, a circulating pump, a circulating water outlet, a solid phase extractant collecting tank, a magnetic holder, an electromagnet, a solid-liquid separation area, a drain valve, a wall sprinkling water inlet, and a wall sprinkling pipe, wherein, the contact reaction chamber is in a conical shape, and utilizes hydraulic power to perform stir to ensure no dead corner exists during contact stir; the obconical solid-liquid separation area increases the action area between a magnetic solid phase extractant and the electromagnet; the solid phase extractant collecting tank is in a downwards protruding dish shape to prevent the solid phase extractant from losing.

10 Claims, 1 Drawing Sheet

PORTABLE EFFICIENT MAGNETIC SOLID PHASE EXTRACTION DEVICE AND EXTRACTION METHOD THEREOF

This application claims priority to Chinese Patent Application Ser. No. CN201610782755.0 filed on 29 Aug. 2016.

TECHNICAL FIELD

The present invention relates to the field of analytical instrument pre-treatment devices, particularly to a portable efficient magnetic solid phase extraction device.

BACKGROUND

The solid phase extraction technology is a sample pre-treatment technology, has the advantages of high efficiency, reliability, small solvent consumption and the like, and has been widely used at present to enrich trace amount of organic contaminants in water in the field of environments and medicines. The current enrichment method mainly adopts a small solid phase extraction column to adsorb contaminants from water via a vacuum pump. However, the existing columnar solid phase extraction technology has a few defects: the offline solid phase extraction requires to enrich and separate target substances through column chromatography, has a great reverse resistance, long extraction time, relatively burdensome operations, and complex steps; a complex environmental sample is easy to cause a column choking phenomenon which seriously influences extraction process and efficiency, such that the requirements for quick water collection and test on site cannot be satisfied at present. Due to the defects above, the quick extraction and test on site are hard to realize under a non-laboratory condition. Compared to the traditional columnar solid phase extraction technology, the appearance of the magnetic solid phase extraction technology taking the magnetic solid phase extractant (patent publication number: CN103435733A) as the core greatly simplifies the sample pre-treatment steps. The magnetic extraction technology on the basis of a magnetic material does not require to tamp the material into a column, avoids the column choking phenomenon, and can quickly enrich and separate large volume of water samples, thus reducing solid phase extraction cost and being easy to realize automation.

In the existing study, the magnetic solid phase extraction generally has no whole set of regular instrument and device. The traditional magnetic reactor is mainly used in the field of water treatment. In practical water treatment, the magnetic reactor has a large size, uses a great many of magnetic materials, and is difficult to separate material by adding an external magnetic field. Therefore, the existing magnetic reactor generally utilizes the excellent settlement performance thereof to realize separation via natural settlement, for example, CN200820237941.7, CN201110125912.8 and CN 201110127627.X. In solid phase extraction, the recovery rate (>99%) of the extractant is the most important factor to ensure the accuracy of the analysis result. In a conventional columnar extraction, the loss of the extractant is effectively prevented via sieve plates at the two ends of the extraction column, thus effectively remaining target substances. However, in the existing magnetic reactor, natural settlement and separation are easy to lose materials, such as pipe residues, reactor wall adsorption, water flow carry and the like. Therefore, the traditional magnetic reactor cannot satisfy the requirement for efficiently separating and recovering magnetic solid phase extractant. Furthermore, the traditional magnetic reactor adopts a split type design without considering the portability of the reactor, and thus cannot be used to perform quick extraction and test on site.

SUMMARY

1. The Problems to be Solved by the Present Invention

Aiming at the problems of solid phase extractant loss, being unfavorable for instant extraction on a field site and the like in existing magnetic solid phase extraction, the present invention provides a portable efficient magnetic solid phase extraction device.

2. Technical Solution

A portable efficient magnetic solid phase extraction device, mainly comprising a contact reaction chamber (1), a circulating water inlet (2), a clear water basin (3), a three-way valve c(4), a water delivery pipe a-1(5-1), a water delivery pipe a-2(5-2), a circulating pump (6), a circulating water outlet (7), a solid phase extractant collecting tank (8), a magnetic holder (9), an electromagnet (10), a solid-liquid separation area (11), a water outlet (12), a three-way valve d(13), a water delivery pipe b-1(14-1), a water delivery pipe b-2(14-2), a drain pipe (15), a drain valve (16), a wall sprinkling water inlet (17), and a wall sprinkling pipe (18), Wherein, the circulating water inlet (2) and the circulating water outlet (7) are respectively located at the upper part and lower part of the contact reaction chamber (1); the circulating water inlet (2) is connected to the three-way valve c(4) via the water delivery pipe a-1(5-1); the circulating water outlet (7) is connected to the three-way valve c(4) via a pipe; the clear water basin (3) is connected to the pipe between the circulating water outlet (7) and the three-way valve c(4) via a pipe;

The lower part of the contact reaction chamber (1) is connected to the solid-liquid separation area (11) via the water outlet (12); the solid phase extractant collecting tank (8), the electromagnet (10), and the magnetic holder (9) are sequentially disposed at the lower part of the solid-liquid separation area (11);

The solid phase extractant collecting tank (8) is connected to the drain valve (16) via a pipe; the drain valve (16) is connected to the drain pipe (15); the sprinkling pipe (18) is located at the upper part inside the contact reaction chamber (1), and is connected to the wall sprinkling water inlet (17); the wall sprinkling water inlet (17) is connected to the three-way valve d(13) via the water delivery pipe b-1(14-1); the three-way valve d(13) is connected to the pipe between the solid phase extractant collecting tank (8) and the drain valve (16) via a pipe; the three-way valve d(13) is connected to the circulating pump (6) via the water delivery pipe b-2(14-2); the circulating pump (6) is connected to three-way valve c(4) via the water delivery pipe a-2(5-2); and the entire device is automatically controlled by a circuit.

Specifically, the contact reaction chamber (1) is made from stainless steel, and is in a conical shape; the circulating water inlet (2) is located 5-8 cm away from the upper edge of the contact reaction chamber (1); the diameters of the circulating water outlet (7) and the circulating water inlet (2) are 2-5 cm.

Specifically, the circulating pump (6) is located at the lower part of the device, and has a pump discharge rate of 16 L/min and a lift of 6 m; water enters the water delivery pipe a-2(5-2) from the circulating water inlet (2), flows through the circulating pump (6), and is sprayed upwards from the circulating water outlet (7) to perform hydraulic stir for 5-30 min.

Specifically, the solid phase extractant collecting tank (8), the magnetic holder (9), the electromagnet (10), and the solid-liquid separation area (11) are located 5-10 cm under the water outlet (12) of the contact reaction chamber (1); the magnetic holder (9) is located undermost; the electromagnet (10) and the solid phase extractant collecting tank (8) are sequentially disposed on the magnetic holder (9), the three of which closely press against each other.

Specifically, the solid-liquid separation area (11) is in an obconical shape, and has a diameter of 8-12 cm.

Specifically, the electromagnet (10) is in a circular shape, and has a diameter of 8-12 cm and a magnetic field strength of 300-1000 Gs.

Specifically, the solid phase extractant collecting tank (8) is in a downwards protruding dish shape; and the left side of the solid phase extractant collecting tank (8) is higher than the right side with a height difference of 1-2 cm.

Specifically, the auxiliary wall sprinkling water inlet (17) is located 2-4 cm away from the upper edge of the contact reaction chamber (1); the wall sprinkling pipe (18) is located on a circumference as high as the wall sprinkling water inlet (17); and 6-10 number of sprinkler heads are uniformly distributed on the wall sprinkling pipe.

Specifically, the clear water basin (3) is located in front of the three-way valve c(4), and has a volume of 100-300 mL.

An efficient magnetic solid phase extraction method, adopting the portable efficient magnetic solid phase extraction device, and mainly comprising the following steps:

(a) Respectively placing a to-be-treated water sample and a magnetic solid phase extractant in the contact reaction chamber (1);

(b) Respectively setting the operating time and drain time of the circulating pump (6), switching on a power supply to start up the circulating pump (6), and enabling mixed solution to flow through the three-way valve c(4) to fully and completely mix the magnetic solid phase extractant with the to-be-treated water sample;

(c) Closing the three-way valve c(4), opening the water outlet (12) and the three-way valve d(13), at the stage of collecting the solid phase extractant, in the solid-liquid separation area (11), collecting the solid phase extractant into the solid phase extractant collecting tank (8) under the action of the electromagnet (10), enabling the treated water sample to flow through the three-way valve d(13) and arrive at the wall sprinkling pipe (18), and flushing a small amount of remaining solid phase extractant into the solid phase extractant collecting tank (8);

(d) Closing the three-way valve d(13), opening the drain valve (16) to discharge the water sample, simultaneously opening the clear water basin (3) and the three-way valve c(4), and utilizing clear water to flush the residual solid phase extractant in the pipe into the solid phase extractant collecting tank (8) for collection; and (e) After the collection is completed, removing the solid phase extractant collecting tank (8), taking out and storing the magnetic solid phase extractant for subsequent elution.

(3) Beneficial Effects

Compared to the existing reactor and technology, the present invention has the following beneficial effects:

(1) The present invention adopts perfect mixing hydraulic stir, is rarely influenced by water turbidity during extraction, has a high extraction efficiency, consumes small power in the process of perfect mixing extraction, and requires short time for extracting large volume of water.

(2) The present invention designs a wall sprinkling pipe in a contact stirring chamber, utilizes extraction water to sprinkle the wall, adds a clear water basin for cleaning, guarantees that no residual solid phase extractant is remained in the device, ensures the recovery rate of the solid phase extractant, and guarantees the accuracy of an extraction result.

(3) Aiming at the advantages of the magnetic solid phase extractant such as small particle diameter, strong magnetism, quick settlement rate and the like, the present invention utilizes an electromagnet to perform separation; and the controllable magnetism of the magnet facilitates the collection and separation of the solid phase extractant.

(4) The present invention adopts an obconical solid-liquid separation area and a dish-shaped solid phase extractant collecting tank, and increases the action area between the magnetic solid phase extractant and the electromagnet, such that the solid phase extractant can be quickly separated from the water.

(5) The present invention is an integrative reaction device, does not require to install complex water inlet and outlet pipes, is simple to operate, can realize automatic operation, and is suitable for large scale sampling in a wild environment.

The mark number in the figures are respectively: 1, contact reaction chamber; 2, circulating water inlet; 3, clear water basin; 4, three-way valve c; 5-1, water delivery pipe a-1; 5-2, water delivery pipe a-2; 6, circulating pump; 7, circulating water outlet; 8, solid phase extractant collecting tank; 9, magnetic holder; 10, electromagnet; 11, solid-liquid separation area; 12, water outlet; 13, three-way valve d; 14-1, water delivery pipe b-1; 14-2, water delivery pipe b-2; 15, drain pipe; 16, drain valve; 17, wall sprinkling water inlet; and 18, wall sprinkling pipe (18).

DETAILED DESCRIPTION

The present reactor will be further described hereafter by combining the drawings.

Figure 1:
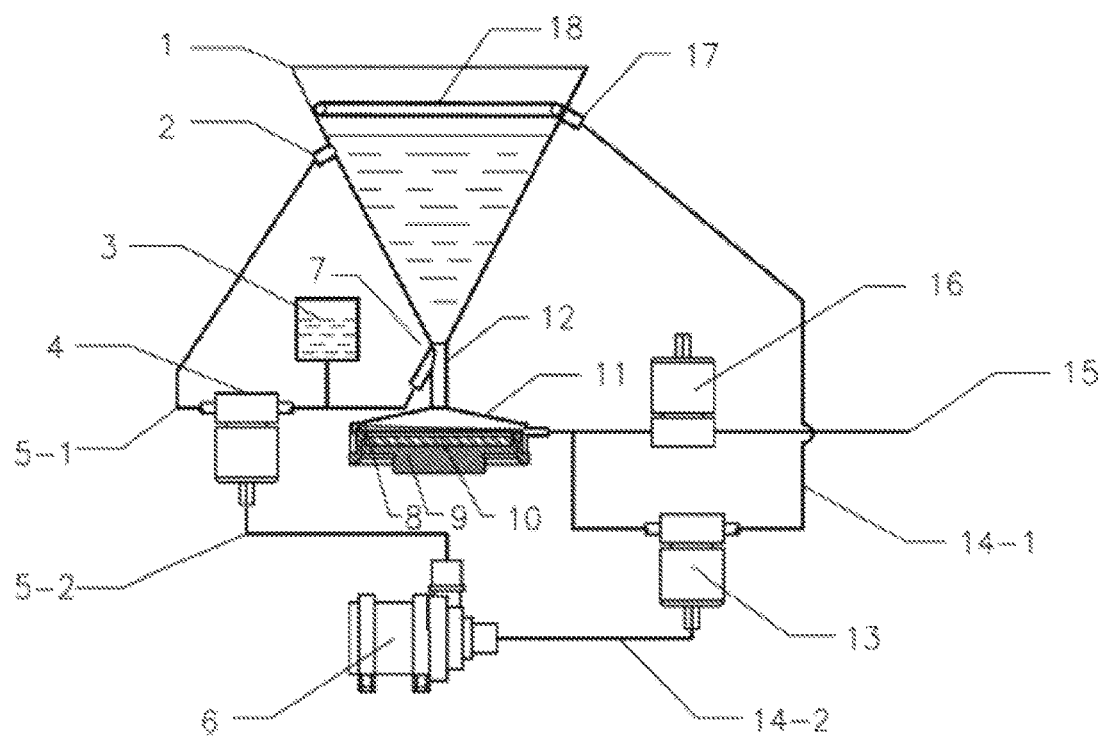
FIG. 1 is a structure diagram of the portable efficient magnetic solid phase extraction device of the present invention.
Figure 2:
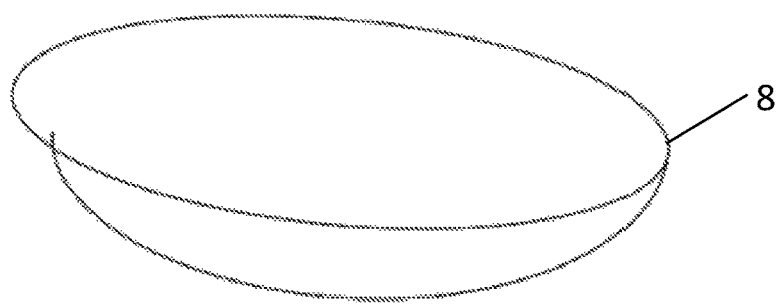
FIG. 2 is a perspective view of the solid phase extractant collecting tank of the present invention.

As shown in FIG. 1-2, a portable efficient magnetic solid phase extraction device, mainly comprising a contact reaction chamber (1), a circulating water inlet (2), a clear water basin (3), a three-way valve c(4), a water delivery pipe a-1(5-1), a water delivery pipe a-2(5-2), a circulating pump (6), a circulating water outlet (7), a solid phase extractant collecting tank (8), a magnetic holder (9), an electromagnet (10), a solid-liquid separation area (11), a water outlet (12), a three-way valve d(13), a water delivery pipe b-1(14-1), a water delivery pipe b-2(14-2), a drain pipe (15), a drain valve (16), a wall sprinkling water inlet (17), and a wall sprinkling pipe (18), Wherein, the circulating water inlet (2) and the circulating water outlet (7) are respectively located at the upper part and lower part of the contact reaction chamber (1); the circulating water inlet (2) is connected to the three-way valve c(4) via the water delivery pipe a-1(5-1); the circulating water outlet (7) is connected to the three-way valve c(4) via a pipe; the clear water basin (3) is connected to the pipe between the circulating water outlet (7) and the three-way valve c(4) via a pipe;

The lower part of the contact reaction chamber (1) is connected to the solid-liquid separation area (11) via the water outlet (12); the solid phase extractant collecting tank (8), the electromagnet (10), and the magnetic holder (9) are sequentially disposed at the lower part of the solid-liquid separation area (11);

The solid phase extractant collecting tank (8) is connected to the drain valve (16) via a pipe; the drain valve (16) is connected to the drain pipe (15); the sprinkling pipe (18) is located at the upper part inside the contact reaction chamber (1), and is connected to the wall sprinkling water inlet (17); the wall sprinkling water inlet (17) is connected to the three-way valve d(13) via the water delivery pipe b-1(14-1); the three-way valve d(13) is connected to the pipe between the solid phase extractant collecting tank (8) and the drain valve (16) via a pipe; the three-way valve d(13) is connected to the circulating pump (6) via the water delivery pipe b-2(14-2); the circulating pump (6) is connected to three-way valve c(4) via the water delivery pipe a-2(5-2); and the entire device is automatically controlled by a circuit.

Wherein,

The contact reaction chamber (1) is made from stainless steel, and is in a conical shape; the circulating water inlet (2) is located 5-8 cm away from the upper edge of the contact reaction chamber (1); the diameters of the circulating water outlet (7) and the circulating water inlet (2) are 2-5 cm.

The circulating pump (6) is located at the lower part of the device, and has a pump discharge rate of 16 L/min and a lift of 6 m; water enters the water delivery pipe a-2(5-2) from the circulating water inlet (2), flows through the circulating pump (6), and is sprayed upwards from the circulating water outlet (7) to perform hydraulic stir for 5-30 min.

The solid phase extractant collecting tank (8), the magnetic holder (9), the electromagnet (10), and the solid-liquid separation area (11) are located 5-10 cm under the water outlet (12) of the contact reaction chamber (1); the magnetic holder (9) is located undermost; the electromagnet (10) and the solid phase extractant collecting tank (8) are sequentially disposed on the magnetic holder (9), the three of which closely press against each other.

The solid-liquid separation area (11) is in an obconical shape, and has a diameter of 8-12 cm.

The electromagnet (10) is in a circular shape, and has a diameter of 8-12 cm and a magnetic field strength of 300-1000 Gs.

The solid phase extractant collecting tank (8) is in a downwards protruding dish shape; and the left side of the solid phase extractant collecting tank (8) is higher than the right side with a height difference of 1-2 cm.

The auxiliary wall sprinkling water inlet (17) is located 2-4 cm away from the upper edge of the contact reaction chamber (1); the wall sprinkling pipe (18) is located on a circumference as high as the wall sprinkling water inlet (17); and 6-10 number of sprinkler heads are uniformly distributed on the wall sprinkling pipe.

The clear water basin (3) is located in front of the three-way valve c(4), and has a volume of 100-300 mL.

A specific application example will be given hereafter.

Extraction of organic matters in water: when in use, adding a to-be-treated water sample 1 L in the contact reaction chamber (1), starting up the circulating pump (6), setting the operating time of the three-way valve c(4) as 30 min, opening the circulating water inlet (7), and closing the water outlet (12); setting the flow rate of the circulating pump (6) as 16 L/min; adding 0.3 g solid phase extractant (activated) in water, hydraulically circulating to fully mix the solid phase extractant with the water; after the contact stir is completed, closing the three-way valve c(4), opening the three-way valve d(13) and the water outlet (12), enabling the mixed solution of the solid phase extractant and the water to flow into the solid-liquid separation area (11), and collecting the solid phase extractant into the solid phase extractant collecting tank (8) under the action of the electromagnet (10); enabling the separated solution to flow through the three-way valve d(13) and arrive at the wall sprinkling water inlet (17), circulating the solution in the wall sprinkling pipe (18), and flushing a small amount of solid phase extractant remained in the contact stirring chamber into the solid-liquid separation area (11); after wall sprinkling is completed, closing the three-way valve d(13), opening the drain valve (16) to discharge the solution after the completion of the solid-liquid separation; after the water is completely discharged, opening the three-way valve c(4), utilizing the clear water in the clear water basin (3) to clean the circulating pump (6) and each water delivery pipe, and ensuring the solid phase extractant to be completely collected; in the process of discharging water, re-opening the circulating pump (6), opening the three-way valve d(13), utilizing the water discharged from the wall sprinkling pipe to flush the small amount of magnetic solid phase extractant remained on the inner wall of the contact reaction chamber (1) into the solid-liquid separation area (11), and enabling the solid phase extractant t be collected; finally, powering off the electromagnet (10), screwing down the magnetic holder (9), taking out the electromagnet (10), taking out the solid phase extractant collecting tank (8), and transferring the solid phase extractant to an elution device. The extraction process of organic contaminants in water is over.

What is claimed is:

1. A portable efficient magnetic solid phase extraction device, characterized in that: the device mainly comprises a contact reaction chamber (1), a circulating water inlet (2), a clear water basin (3), a three-way valve c(4), a water delivery pipe a-1(5-1), a water delivery pipe a-2(5-2), a circulating pump (6), a circulating water outlet (7), a solid phase extractant collecting tank (8), a magnetic holder (9), an electromagnet (10), a solid-liquid separation area (11), a water outlet (12), a three-way valve d(13), a water delivery pipe b-1(14-1), a water delivery pipe b-2(14-2), a drain pipe (15), a drain valve (16), a wall sprinkling water inlet (17), and a wall sprinkling pipe (18), wherein, the circulating water inlet (2) and the circulating water outlet (7) are respectively located at the upper part and lower part of the contact reaction chamber (1); the circulating water inlet (2) is connected to the three-way valve c(4) via the water delivery pipe a-1(5-1); the circulating water outlet (7) is connected to the three-way valve c(4) via a pipe; the clear water basin (3) is connected to the pipe between the circulating water outlet (7) and the three-way valve c(4) via a pipe; the lower part of the contact reaction chamber (1) is connected to the solid-liquid separation area (11) via the water outlet (12); the solid phase extractant collecting tank (8), the electromagnet (10), and the magnetic holder (9) are sequentially disposed at the lower part of the solid-liquid separation area (11);

the solid phase extractant collecting tank (8) is connected to the drain valve (16) via a pipe; the drain valve (16) is connected to the drain pipe (15); the sprinkling pipe (18) is located at the upper part inside the contact reaction chamber (1), and is connected to the wall sprinkling water inlet (17); the wall sprinkling water inlet (17) is connected to the three-way valve d(13) via the water delivery pipe b-1(14-1); the three-way valve d(13) is connected to the pipe between the solid phase extractant collecting tank (8) and the drain valve (16)

via a pipe; the three-way valve d(13) is connected to the circulating pump (6) via the water delivery pipe b-2 (14-2); the circulating pump (6) is connected to three-way valve c(4) via the water delivery pipe a-2(5-2); and the entire device is automatically controlled by a circuit.

2. The portable efficient magnetic solid phase extraction device as claimed in claim 1, characterized in that: the contact reaction chamber (1) is made from stainless steel, and is in a conical shape; the circulating water inlet (2) is located 5-8 cm away from the upper edge of the contact reaction chamber (1); the diameters of the circulating water outlet (7) and the circulating water inlet (2) are 2-5 cm.

3. The portable efficient magnetic solid phase extraction device as claimed in claim 1, characterized in that: the circulating pump (6) is located at the lower part of the device, and has a pump discharge rate of 16 L/min and a lift of 6 m; water enters the water delivery pipe a-2(5-2) from the circulating water inlet (2), flows through the circulating pump (6), and is sprayed upwards from the circulating water outlet (7) to perform hydraulic stir for 5-30 min.

4. The portable efficient magnetic solid phase extraction device as claimed in claim 1, characterized in that: the solid phase extractant collecting tank (8), the magnetic holder (9), the electromagnet (10), and the solid-liquid separation area (11) are located 5-10 cm under the water outlet (12) of the contact reaction chamber (1); the magnetic holder (9) is located undermost; the electromagnet (10) and the solid phase extractant collecting tank (8) are sequentially disposed on the magnetic holder (9), the three of which closely press against each other.

5. The portable efficient magnetic solid phase extraction device as claimed in claim 1, characterized in that: the solid-liquid separation area (11) is in an obconical shape, and has a diameter of 8-12 cm.

6. The portable efficient magnetic solid phase extraction device as claimed in claim 1, characterized in that: the electromagnet (10) is in a circular shape, and has a diameter of 8-12 cm and a magnetic field strength of 300-1000 Gs.

7. The portable efficient magnetic solid phase extraction device as claimed in claim 1, characterized in that: the solid phase extractant collecting tank (8) is in a downwards protruding dish shape; and the left side of the solid phase extractant collecting tank (8) is higher than the right side with a height difference of 1-2 cm.

8. The portable efficient magnetic solid phase extraction device as claimed in claim 1, characterized in that: an auxiliary wall sprinkling water inlet (17) is located 2-4 cm away from the upper edge of the contact reaction chamber (1); the wall sprinkling pipe (18) is located on a circumference as high as the wall sprinkling water inlet (17); and 6-10 number of sprinkler heads are uniformly distributed on the wall sprinkling pipe.

9. The portable efficient magnetic solid phase extraction device as claimed in claim 1, characterized in that: the clear water basin (3) is located in front of the three-way valve c(4), and has a volume of 100-300 mL.

10. An extraction method of the portable efficient magnetic solid phase extraction device as claimed in claim 1, characterized in that: the method adopts the portable efficient magnetic solid phase extraction device, and comprises the steps of:
(a) placing a to-be-treated water sample and a magnetic solid phase extractant in the contact reaction chamber (1), respectively;
(b) setting the operating time and drain time of the circulating pump (6), switching on a power supply to start up the circulating pump (6), and enabling mixed solution to flow through the three-way valve c(4) to fully and completely mix the magnetic solid phase extractant with the to-be-treated water sample, respectively;
(c) closing the three-way valve c(4), opening the water outlet (12) and the three-way valve d(13), at the stage of collecting the solid phase extractant, in the solid-liquid separation area (11), collecting the solid phase extractant into the solid phase extractant collecting tank (8) under the action of the electromagnet (10), enabling the treated water sample to flow through the three-way valve d(13) and arrive at the wall sprinkling pipe (18), and flushing a small amount of remaining solid phase extractant into the solid phase extractant collecting tank (8);
(d) closing the three-way valve d(13), opening the drain valve (16) to discharge the water sample, simultaneously opening the clear water basin (3) and the three-way valve c(4), and utilizing clear water to flush the residual solid phase extractant in the pipe into the solid phase extractant collecting tank (8) for collection; and
(e) after the collection is completed, removing the solid phase extractant collecting tank (8), taking out and storing the magnetic solid phase extractant for subsequent elution.

* * * * *